US009168287B2

(12) United States Patent
Shirvan et al.

(10) Patent No.: US 9,168,287 B2
(45) Date of Patent: Oct. 27, 2015

(54) ACTIVATED LEUKOCYTE CONDITIONED SUPERNATANT AND USES FOR WOUND HEALING

(75) Inventors: Mitchell Shirvan, Herzliyya (IL); Eilat Bain, Rehovot (IL); Marina Bubis, Rehovot (IL); Irene Ginis, Belt Shemesh (IL)

(73) Assignee: MacroCure, Ltd., Petach Tikva (IL)

( * ) Notice: Subject to any disclaimer, the term of this patent is extended or adjusted under 35 U.S.C. 154(b) by 0 days.

(21) Appl. No.: 13/821,676

(22) PCT Filed: Sep. 8, 2011

(86) PCT No.: PCT/IB2011/002756
§ 371 (c)(1),
(2), (4) Date: May 16, 2013

(87) PCT Pub. No.: WO2012/032418
PCT Pub. Date: Mar. 15, 2012

(65) Prior Publication Data
US 2013/0224148 A1    Aug. 29, 2013

Related U.S. Application Data

(60) Provisional application No. 61/381,296, filed on Sep. 9, 2010.

(51) Int. Cl.
*A61K 38/20* (2006.01)
*A61L 15/32* (2006.01)
*A61K 35/15* (2015.01)
*A61K 35/17* (2015.01)
*A61L 15/40* (2006.01)
*A61L 15/44* (2006.01)
*A61L 26/00* (2006.01)
*A61L 27/38* (2006.01)
*A61L 27/54* (2006.01)
*A61K 35/16* (2015.01)
*A61K 38/19* (2006.01)
*A61L 15/42* (2006.01)

(52) U.S. Cl.
CPC ............ *A61K 38/2053* (2013.01); *A61K 35/15* (2013.01); *A61K 35/16* (2013.01); *A61K 35/17* (2013.01); *A61K 38/191* (2013.01); *A61K 38/204* (2013.01); *A61L 15/32* (2013.01); *A61L 15/40* (2013.01); *A61L 15/42* (2013.01); *A61L 15/44* (2013.01); *A61L 26/0057* (2013.01); *A61L 26/0066* (2013.01); *A61L 27/3804* (2013.01); *A61L 27/54* (2013.01); *A61L 2300/41* (2013.01); *A61L 2300/412* (2013.01); *A61L 2300/64* (2013.01)

(58) Field of Classification Search
CPC . A61K 2300/00; A61K 35/15; A61K 38/191; A61K 38/204; A61K 38/2053; A61K 35/545; A61K 51/1203; A61K 38/18; A61K 8/02; A61K 8/0208; C12P 21/00
See application file for complete search history.

(56) References Cited

U.S. PATENT DOCUMENTS

| 4,986,979 | A | 1/1991 | Morgan et al. |
| 5,981,282 | A | 11/1999 | Ryan |
| 6,146,890 | A * | 11/2000 | Danon .......................... 435/377 |
| 6,372,494 | B1 * | 4/2002 | Naughton et al. ............ 435/391 |
| 8,367,799 | B2 | 2/2013 | Tsunoda et al. |
| 2006/0210543 | A1 | 9/2006 | Leor et al. |
| 2008/0050830 | A1 | 2/2008 | Floriano et al. |
| 2012/0316906 | A1 | 12/2012 | Hampapur et al. |
| 2013/0071465 | A1 | 3/2013 | Shirvan et al. |
| 2015/0030635 | A1 | 1/2015 | Ginis et al. |
| 2015/0071892 | A1 | 3/2015 | Ginis et al. |

FOREIGN PATENT DOCUMENTS

| EP | 1 731 175 | 12/2006 |
| GB | 2 146 523 | 4/1985 |
| JP | 2010-259134 | 9/1998 |
| JP | 2004-041141 | 2/2004 |
| RU | 2 143 685 | 12/1999 |
| RU | 2143693 C1 | 12/1999 |
| RU | 2283129 C1 | 9/2006 |
| WO | WO 89/07445 | 8/1989 |
| WO | WO 96/01045 | 1/1996 |
| WO | WO 00/69449 | 11/2000 |
| WO | WO 03/044037 | 5/2003 |
| WO | WO 2008/155659 | 12/2008 |
| WO | WO 2010/100570 | 12/2010 |
| WO | WO 2012/032418 | 3/2012 |

OTHER PUBLICATIONS

Koch et al, Science. Dec. 11, 1992;258(5089):1798-801.*
Salmon-Err et al., Lab. Invest. 80:1337-1343, (2000).*
Vissers et al., J Immunol Methods. Jun. 13, 1988;110(2):203 Abstract only.*
International Preliminary Report on Patentability and Written Opinion for International Patent Application No. PCT/IB2011/002756, dated Apr. 26, 2012 (14 pages).
Patent Search Report for Eurasian Application No. 201390314, dated Aug. 8, 2013 (1 page).
Frenkel et al., "Activation of human monocytes/macrophages by hypo-osmotic shock," Clinical and Experimental Immunology, vol. 124, No. 1, Apr. 2001, pp. 103-109, XP009157316 (7 pages).
Werner et al., "Regulation of wound healing by growth factors and cytokines," Physiological Reviews, vol. 38, No. 3, Jul. 2003, pp. 835-870, XP002672025 (38 pages).
Fonder et al., "Treating the chronic wound: A practical approach to the care of nonhealing wounds and wound care dressings," Journal of the American Academy of Dermatology, vol. 58, No. 2, Jan. 17, 2008, pp. 185-206 (22 pages).

(Continued)

*Primary Examiner* — Daniel C Gamett
(74) *Attorney, Agent, or Firm* — Finnegan, Henderson, Farabow, Garrett & Dunner, LLP

(57) ABSTRACT

Disclosed are therapeutic, activated leukocyte conditioned supernatants, methods of making them, and methods of using the conditioned supernatants to repair or promote healing of wounds.

12 Claims, 2 Drawing Sheets

(56) References Cited

OTHER PUBLICATIONS

Frenkel, O. et al., "Activated macrophages for treating skin ulceration: gene expression in human monocytes after hypo-osmotic shock," *Clin. and Experimental Immunol.*, vol. 128, No. 1, pp. 59-66 (2002).

Danon, D. et al., "Treatment of Human Ulcers by Application of Macrophages Prepared from a Blood Unit," *Experimental Gerontol.*, Aug. 7, 1997, vol. 32, No. 6, pp. 633-641.

Orenstein, A. et al., "Treatment of deep sternal wound infections post-open heart surgery by application of activated macrophage suspension," *Wound Repair and Regeneration*, May-Jun. 2005, vol. 13, No. 3, pp. 237-242.

Zuloff-Shani, A. et al., "Macrophage suspensions prepared from a blood unit for treatment of refractory human ulcers," *Transfusion and Apheresis Science*, vol. 30, pp. 163-167 (2004).

Zuloff-Shani, A. et al., "Hard to heal pressure ulcers (stage III-IV): Efficacy of injected activated macrophage suspension (AMS) as compares with standard of care (SOC) treatment controlled trial,"*Archives of Gerontol. and Geriatrics*, Nov. 20, 2009, pp. 267-272.

Melichar, B. et al., "Hepatic Arterial Administration of Activated Leukocytes in Patients with Liver Metastasis," *Cancer Biol. & Radiopharmaceuticals*, vol. 17, No. 5, pp. 545-552 (2002).

Werner, S. et al., "Regulation of Wound Healing by Growth Factors and Cytokines," *Physiological Reviews*, vol. 83, No. 3, Jul. 2003, pp. 835-872.

International Search Report and Written Opinion for International Application No. PCT/IB2010/000882, dated Oct. 27, 2010 (11 pages).

International Search Report and Written Opinion for International Application No. PCT/IB2011/002756, dated Apr. 26, 2012 (14 pages).

International Search Report from the European Patent Office for International Application No. PCT/IB2013/000848, dated Jul. 4, 2013 (4 pages).

International Search Report from the European Patent Office for International Application No. PCT/IB2013/000935 dated Jul. 9, 2013 (3 pages).

Koski, G. et al., "Reengineering dendritic cell-based anti-cancer vaccines," *Immunological Reviews*, vol. 222, pp. 256-276 (2008).

Reddy, A. et al., "A Monocyte Conditioned Medium Is More Effective Than Defined Cytokines in Mediating the Terminal Maturation of Human Dendritic Cells," *Blood*, vol. 90, pp. 3640-3646 (1997).

Leor, J. et al., "Ex Vivo Activated Human Macrophages Improve Healing, Remodeling, and Function of the Infarcted Heart," *Circulation*, vol. 114, pp. I-94-I-100 (2006).

Patham, B. et al., "Advances in Dendritic Cell-Based Vaccines for HIV," *Current Medicinal Chem.*, vol. 18, pp. 3987-3994 (2011).

Shi, M. et al., "Hepatitis B virus (HBV) antigen-pulsed monocyte-derived dendritic cells from HBV-associated hepatocellular carcinoma patients significantly enhance specific T cell responses in vitro," *Clin. and Experimental Immunol.*, vol. 147, pp. 277-286 (2006).

\* cited by examiner

ACTIVATED LEUKOCYTE CONDITIONED SUPERNATANT AND USES FOR WOUND HEALING

CROSS-REFERENCE TO RELATED APPLICATIONS

This application claims benefit of Provisional Application Ser. No. 61/381,296, filed Sep. 9, 2010, the disclosure of which is incorporated herein by reference.

BACKGROUND OF THE INVENTION

The wound healing process involves participation of white blood cells, also known as leukocytes. Leukocytes include granulocytes, monocytes and lymphocytes. Among the different types of granulocytes are neutrophils, basophils and eosinophils. Monocytes differentiate into macrophages, which are responsible for engulfment of tissue debris or invading foreign substances. Three common types of lymphocytes are T-cells, B-cells and natural killer cells. T-cells and B-cells play important roles in the recognition of antigens in the body (Parkin, 2001). Natural killer (NK) cells identify infected cells by alterations in the levels of the major histocompatability complex (MHC), and destroy the infected cells (Moretta, 2008).

The process of wound healing occurs in three overlapping phases. (Li, 2007; Broughton, 2006; Tsirogianni, 2006; Singer, 1999; Martin, 1997). The first phase is the inflammatory phase. It is characterized by recruitment of neutrophils, followed by monocytes to the wound site, where they kill and phagocytize bacteria (Agaiby, 1999).

The second wound healing phase which is known as the proliferative phase, involves formation of new granulation tissue. Fibroblasts proliferate and migrate into the wound space and synthesize collagen and other components of extracellular matrix (Greiling, 1997). At the same time, angiogenesis occurs, providing nutrients and oxygen to the metabolically active new granulation tissue (Tonnesen, 2000). Keratinocytes from the intact epidermis start to migrate over the provisional matrix and begin to proliferate, leading the way for new epithelial tissue (Kim, 1992).

Remodeling is the third and final phase in wound healing. It is characterized by fibroblast differentiation into myofibroblasts, which contract and bring the wound edges closer together (Tomasek, 2002). Remodeling of the collagen fibers by degradation and re-synthesis allows the wound to gain strength by re-orientation of the collagen fibers (a process tightly controlled by growth factors) (Werner, 2003).

The participation of leukocytes in the healing process is largely associated with their production of cytokines and growth factors (Keen, 2008). Recruitment of leukocyte subsets is regulated by chemoattractant cytokines (chemokines) such as interleukin (IL)-8, growth-regulated protein alpha (GRO-a), and monocyte chemotactic protein-1 (MCP-1) that activate and selectively guide various leukocyte subsets to wounds (Rossi and Zlotnik, 2000). Granulocytes produce proteases and reactive oxygen intermediates Macrophages produce proinflammatory cytokines and growth factors (Riches, 1996). Proinflammatory cytokines, including interleukins 1-alpha and 1-beta (IL-1-alpha and IL-1-beta), IL-6, and tumor necrosis factor (TNF)-alpha, play an important role both at the inflammatory and proliferative phase of wound repair. These cytokines also regulate the immune response. Angiogenesis is potentiated by hypoxia, nitric oxide (NO), VEGF and fibroblast growth factor 2 (FGF-2) (Liekens, 2001). TGF-beta contributes to the fibrotic process by recruiting fibroblasts and stimulating their synthesis of collagens I, III, and V, proteoglycans, fibronectin and other ECM components. TGF-beta concurrently inhibits proteases (C. U. Niesler, and M. W. J. Ferguson, 2001). PDGF, which is released by platelets and also by activated macrophages, endothelial cells and fibroblasts, is a major player in regulating fibroblast and smooth muscle cell recruitment and proliferation (C. H. Heldin and B. Westermark, 1999). Similarly lymphocytes, besides being immunological effector cells, also produce growth factors (Blotnik, 1994), and contribute to tissue remodeling during the late phase of wound healing.

The challenge of treating wounds is often compounded by patients with multiple pathologies such as diabetes, coronary artery disease and hypertension. These diseases have the common effect of exacerbating vascular complications due to various physiological conditions. Complications from wounds may result in increased morbidity and mortality (Doshi, 2008).

Conventional wound treatments include surgical debridement, antibiotic therapies and various dressings (Moran, 2008; Fonder, 2008). Wounds resistant to conventional treatment are also referred to as refractory wounds. These wounds lead to a decrease in quality of life and can result in increased morbidity and mortality. Thus, a need continues to exist for effective compositions and methods for wound healing.

SUMMARY OF THE INVENTION

One aspect of the present invention is directed to a method for making a substantially cell-free supernatant conditioned by activated leukocytes-activated leukocyte conditioned supernatant ("ALCS"). In some embodiments, the method includes the steps of a) incubating human leukocytes under conditions of time and temperature (e.g., for about 90 minutes to about 24 hours at a temperature from about room temperature to about 37° C., and in some embodiments is for about 8 to about 20 hours at room temperature) to activate the leukocytes (also referred to herein as the first incubation); b) subjecting the leukocytes to hypo-osmotic shock (e.g., by contacting the leukocytes with a physiologically acceptable aqueous solution such as distilled water); c) adding to the leukocytes of step b, a physiologically acceptable salt solution in an amount effective to restore isotonicity; d) mixing the leukocytes of step c with a medium such as serum (which may be obtained from the same or a different blood sample as the leukocytes) to form an incubation composition; e) incubating the composition under conditions of time and temperature to condition the medium, thus producing the ALCS (also referred to herein as the second incubation); and f) separating at least some of the leukocytes and other cellular matter from the incubation composition of e), so as to produce a substantially cell-free ALCS.

In another embodiment, the invention is directed to a method for making a substantially cell-free, activated leukocyte-conditioned supernatant (ALCS), comprising the steps of: a) incubating human leukocytes under conditions of time and temperature to activate the leukocytes; b) subjecting the leukocytes to hypo-osmotic shock; c) adding to the leukocytes of step b) a salt solution in an amount which restores isotonicity, then separating the leukocytes from the resulting solution; d) mixing the leukocytes of step c) with serum to form an incubation composition; e) incubating the incubation composition under conditions of time and temperature to increase the concentration of at least one cytokine or growth factor in the incubation composition; and f) separating the leukocytes and other cellular matter from the incubation composition of e), so as to produce a substantially cell-free ALCS.

In some embodiments, the incubation of step a) occurs at a temperature of about 12° C. to about 28° C. for a time ranging from about 8 to about 20 hours. In other embodiments, the incubation of step a) occurs at a temperature of about 18° C. to about 24° C. for a time ranging from about 8 to about 12 hours. In still other embodiments, the incubation of step a) occurs at a temperature of 12° C. to about 28° C. for a time ranging from about 90 minutes upwards of 2, 3, 4, 5, 6, 7, 8, or 12 to about 20 hours. In yet other embodiments, the incubation of step a) occurs at a temperature up to about 37° C. and for a time ranging from five hours to about 24 hours.

In some embodiments, step a) is conducted in a container to which leukocytes adhere and/or which contains a scaffold comprising leukocyte agonists or adhesion molecules.

In some embodiments, step b) comprises contacting the leukocytes with water or a hypotonic salt solution for about 25 to about 45 seconds.

In some embodiments, the leukocytes of a) and the serum of d) are obtained from the same donor. In other embodiments, the leukocytes of a) and the serum of d) are obtained from different donors.

In some embodiments, the serum of d) is obtained by g) contacting a separate sample of human plasma with a coagulating agent, wherein the plasma and the leukocytes of a) may be obtained from the same or different donors, and h) removing coagulated solids, wherein the contacting in g) is conducted substantially contemporaneously with the incubating of a). In certain, the serum of g) is frozen prior to contacting the leukocytes. Further, in certain embodiments, the plasma is obtained from an AB+ donor. In certain embodiments, the coagulating agent is CaCl$_2$.

In still other embodiments, the invention is directed to a method of making a substantially cell-free ALCS activated leukocyte-conditioned supernatant (ALCS), comprising: a) obtaining activated leukocytes; b) contacting the activated leukocytes with an incubation medium to form an incubation composition; c) incubating the incubation composition at a temperature and time sufficient to increase the concentration of at least one cytokine or growth factor in the incubation composition; and d) removing leukocytes from the incubation composition to produce a substantially cell-free ALCS activated leukocyte-conditioned supernatant (ALCS).

In any of the embodiments directed to a method of making an ALCS, the incubation composition may be incubated at room temperature for a time of about 8 to about 18 hours up to 72 hours. Alternatively, the incubation composition may be incubated at about 37° C. for a time of about 1 to about 5 hours.

In addition, in any of the embodiments directed to a method of making an ALCS, the method may further comprise freezing, lyophilizing or freeze-drying the ALCS.

Likewise, in any of the embodiments directed to a method of making an ALCS, the method may further comprise mixing the leukocytes remaining following preparation of a first ALCS with a second serum or other physiologic medium to form a second incubation composition; incubating the second incubation composition under conditions of time and temperature to increase the concentration of at least one cytokine or growth factor in the incubation composition, thus producing a second sample of the ALCS; and separating the leukocytes and other cellular matter from the second incubation composition of so as to produce a second sample of the substantially cell-free ALCS.

In those embodiments utilizing serum, the serum may be obtained from a sample of plasma, which may be obtained from the same or a different whole blood sample (i.e., from the same or a different human), that has been contacted with a coagulating agent at about 37° C. In some embodiments, the contacting may be for a time substantially concurrent with the incubation of the leukocytes in a), followed by separating serum from the coagulated plasma sample. In other embodiments, the serum or plasma is obtained from a commercial or non-profit supplier and may be either fresh or in a storage-compatible form, such as frozen.

In some embodiments, the conditioning of the supernatant by the activated leukocytes is carried out under conditions of time and temperature generally ranging for about 1 hour to about 18 hours, and at about 22° C. to about 37° C.

In another aspect, the invention is directed to a substantially cell-free activated leukocyte-conditioned supernatant produced by a method of the invention.

In still another aspect, the invention is directed to a substantially cell-free activated leukocyte-conditioned supernatant comprising at least about 1000 pg/mL human IL-8, at least about 10-20 pg/mL human IL-6, and at least about 20 pg/mL human TNFalpha.

In other aspects, the invention is directed to any of the substantially cell-free activated leukocyte-conditioned supernatants of the invention for use in treating a wound. In some embodiments, the wound is a decubital ulcer, a pressure ulcer, a lower extremity ulcer, tendonitis, a deep sternal wound, a post-operative wound, a refractory post-operative wound of the trunk area, a wound to the great saphenous vein following harvesting of the great saphenous vein, a venous ulcer, a burn wound, a battlefield wound, or an anal fissure. In some embodiments, the lower extremity ulcer is in a diabetic patient. In some embodiments, the wound is a venous ulcer, pressure ulcer, or post-operative ulcer.

In other aspects, the invention is directed to any of the substantially cell-free activated leukocyte-conditioned supernatants of the invention for inhibiting the onset of infection in a wound. In some embodiments, the wound is caused by trauma. In certain embodiments, the trauma is caused by surgery.

Another aspect of the present invention is directed to a method of treating a wound, also referred to as promoting wound healing, which includes administering or otherwise applying a substantially cell-free, activated leukocyte-conditioned serum (ALCS) as described herein (including ALCS produced by the methods of making described herein), or an article of manufacture comprising the ALCS and a dressing, scaffold, or matrix, to a wound. Accordingly, the invention is also directed to the use of a substantially cell-free ALCS as described herein (including ALCS produced by the methods of making described herein), or an article of manufacture comprising the ALCS and a dressing, scaffold, or matrix, in methods of treating a wound or promoting wound healing.

In some embodiments, the wound is a decubital ulcer, a pressure ulcer, a lower extremity ulcer, tendonitis, a deep sternal wound, a post-operative wound, a refractory post-operative wound of the trunk area, a wound to the great saphenous vein following harvesting of the great saphenous vein, a venous ulcer, a burn wound, a battlefield wound, or an anal fissure. In some embodiments, the lower extremity ulcer is in a diabetic patient. In some embodiments, the wound is a venous ulcer, pressure ulcer, or post-operative ulcer.

Another aspect of the present invention is directed to a method for inhibiting the onset of infection in a wound, which includes administering or otherwise applying a substantially cell-free, activated leukocyte-conditioned serum (ALCS) as described herein (including ALCS produced by the methods of making described herein), or an article of manufacture comprising the ALCS and a dressing, scaffold, or matrix, to a wound. Accordingly, the invention is also directed to the use of a substantially cell-free ALCS as described herein (including ALCS produced by the methods of making described herein), or an article of manufacture comprising the ALCS and a dressing, scaffold, or matrix, in methods inhibiting the onset of infection in a wound.

In some embodiments, the wound is caused by trauma. In certain embodiments, the trauma is caused by surgery.

In any of the embodiments involving application of an ALCS of the invention to a wound, the ALCS may be injected into the wound, injected into tissue surrounding the wound, applied to an open wound, or applied to the wound via a dressing. In addition, in any of the embodiments involving application of an ALCS of the invention to a wound, the ALCS may be derived from an autologous blood sample or from an allogeneic blood sample.

In other aspects, the invention is directed to an article of manufacture comprising a substantially cell-free activated leukocyte-conditioned supernatant of the invention and a dressing, scaffold, or matrix. In some embodiments, the dressing is gauze, a bandage, a non-adhesive mesh, a membrane, foils, foam, or a tissue adhesive. In other embodiments, the dressing is a moisture-keeping barrier chosen from a paste, a cream, an ointment, a nonpermeable or semi-permeable membrane or foil, a hydrocolloid, a hydrogel, or combinations thereof. In still other embodiments, the dressing is an antimicrobial dressing.

In those embodiments involving a scaffold or matrix, the scaffold or matrix may be a solid before implantation. Alternatively, the scaffold or matrix may be a gel that solidifies following implantation.

As the terms are used herein, "conditioning" of the supernatant and "conditioned supernatant", refer to a supernatant having a concentration of cytokines (at least IL-8) and growth factors greater than normal physiological levels and which is effective for wound healing. Step 0 of separating the leukocytes may be carried out via centrifugation, or sedimentation by gravitation which causes the leukocytes to aggregate in the form of a cellular pellet which can be easily separated from the liquid fraction, to prepare one embodiment of a substantially cell-free, activated leukocyte conditioned supernatant.

The present invention provides several advantages, including, for example, an effective wound-healing composition that contains high concentrations of cytokines and growth factors but which is substantially cell-free. This feature allows for concerted use of anesthetics and other drugs useful for wound healing that might otherwise adversely interact with leukocytes. The substantially cell-free nature of the composition also further reduces likelihood of deleterious side effects caused by immune cells such as granulocytes and lymphocytes. Therefore higher concentrations of leukocytes can be used to condition the supernatant, to increase the amount of biologically active agonists in it. The compositions can be made without stringent criteria for donor-patient matching in terms of starting materials. The compositions are amenable to freezing or lyophilization thus providing longer shelf-life and versatility in terms of use. For example, a portion of one batch can be frozen and used for additional administrations, and thus avoid the need to obtain additional blood from the same donor. This feature also provides a more uniform and safer product. Moreover, after removal from the liquid fraction, the activated leukocytes may be used to condition a new portion of serum, immediately or after a short storage. Thus, the method allows for reuse of the activated leukocytes for preparation of additional batches of conditioned serum.

DETAILED DESCRIPTION

Figure 1:
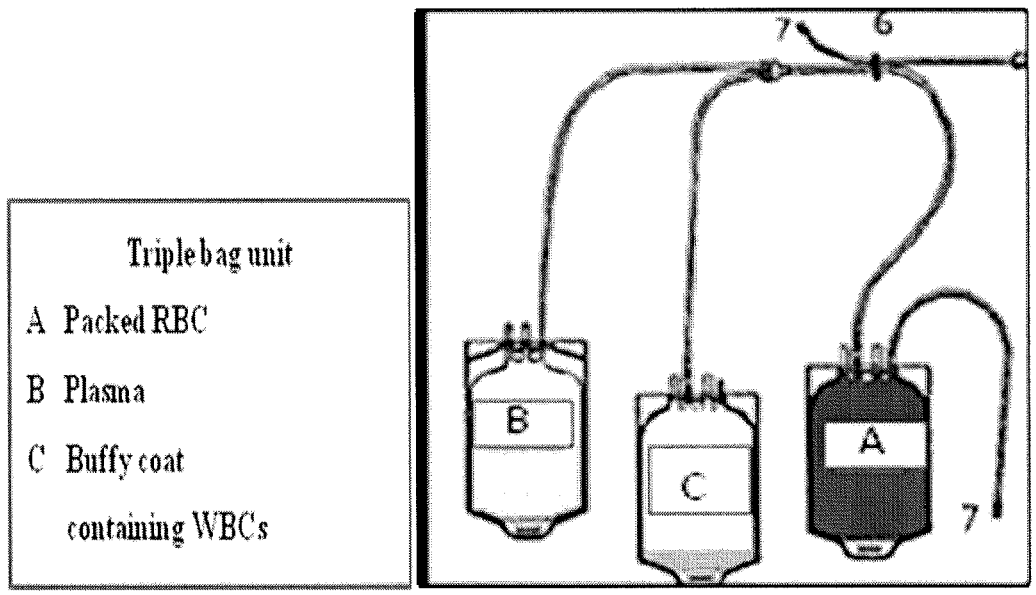
FIG. 1 schematically depicts a first portion of a representative system for producing the ALC compositions of the present invention, which includes bags A-C (Set-1), which are blood storage bags or containers, wherein bag A contains packed red blood cells collected from a donor; bag B contains plasma; and bag C contains leukocytes (which following initial separation from whole blood forms a layer commonly referred to as the buffy coat).

Blood is defined herein as whole blood or any of its constituent parts (e.g., plasma, leukocytes, platelets or red blood cells). The amounts of soluble factors that may be present in the ALCS of the present invention may be lower or higher than that in whole blood.

The term "about" as used herein in connection with any and all values (including lower and upper ends of numerical ranges) as any value having an acceptable range of deviation of +/−0.5% to +/−20% (and values there between, e.g., ±1%, ±1.5%, ±2%, ±2.5%, ±3%, ±3.5%, ±4%, ±4.5%, ±5%, ±5.5%, ±6%, ±6.5%, ±7%, ±7.5%, ±8%, +8.5%, ±9%, ±9.5%, ±10%, ±10.5%, ±11%, ±11.5%, ±12%, ±12.5%, ±13, ±13.5%, ±14%, ±14.5%, ±15%, ±15.5%, ±16%, ±16.5%, ±17%, ±17.5%, ±18%, ±18.5%, ±19%, ±19.5%, and ±20%).

As used herein and in the appended claims, the singular forms "a," "an," "or," and "the" include plural referents unless the context clearly dictates otherwise.

The starting materials for practicing the inventive methods may be obtained from several sources. Whole blood or one or more components thereof (e.g., leukocytes and plasma) may be obtained from autologous or allogeneic sources. In one embodiment of the present invention, a blood sample is collected from the patient who will ultimately be treated with the ALCS, which is referred to herein as an autologous blood sample or source. In embodiments wherein the source(s) i.e., the blood or its components, is obtained from an individual other than the intended ALCS recipient, which is referred to as an allogeneic blood sample or source, these starting materials may be conveniently obtained from a blood bank. The samples may be screened by the blood bank for irregular antibodies to red cell antigens, and transfusion-transmittable diseases. More specifically, screening can be conducted with antibodies using an Abbott PRISM instrument against: Hepatitis B, C, HIV 1/2, HTLV and Syphilis (−HCV; HbsAg; anti-HIV 1/2 O+; and anti-HTLV I/II). The samples can also be screened for HIV, HCV and HBV by molecular methods (NAT-Nucleic Acid Testing). Molecular screening can be accomplished using commercially available instrumentation, e.g., the TIGRIS system of Chiron.

In those embodiments involving allogeneic sources, the samples can be obtained from donors with the same blood type as the intended ALCS recipient. In other embodiments, the sample may be obtained from a donor with any blood type, including a blood type that is different from the intended ALCS recipient. For example, since the leukocytes are substantially removed in the course of preparing the ALCS, when plasma or serum is used it may be obtained from alternative sources such as donors with AB+ blood, who are universal donors for plasma and serum. The plasma and/or serum can be fresh, stored (e.g., at 1-6° C. for less than 24 hours), dried, or otherwise pre-treated (e.g., pathogen-reduced plasma and/or serum and solvent/detergent (SD) treated plasma and/or serum). The plasma used to make some embodiments of the present invention can be fresh or stored at 1-6° C. for less than 24 hours, or Fresh Frozen Plasma, or Dried Plasma, or Pathogen-Reduced Plasma, or Solvent/Detergent (SD) Treated Plasma. The leukocytes can be obtained from patients with any blood type. Regardless of the source, all necessary processing of the sample(s) can be carried out without the need for highly specialized equipment.

Exemplary embodiments of making the ALCS composition of the present invention are now described with reference to FIGS. 1 and 2, which illustrate a system containing two sets of interconnected sterile bags. The system is sealed so that there is no exposure to the outside environment. Specifically, the tubes connecting the two sets are welded together, that is, joined, to form one system using a Sterile Connecting Device (e.g., TSCD®-II Cat number ME-203AH of Terumo). More specifically, to ensure compliance with sterility standards, the welding and cutting of the tubes is done by pre-heating special wafers, typically at about 300° C. (although sterility can be effectively achieved by pre-heating at lower or even higher temperatures). This high temperature increases the sterility of the welding procedure. To further ensure sterility, the welding may be performed in a class 100 Biological Safety Cabinet within a class 100,000 containment area.

As illustrated in these figures, the system contains two sterile bag sets. Set 1, containing bags A, B, and C, is a standard, commercially available triple bag set commonly used for blood transfusion. A human blood sample, typically in the volume of about 400 to about 550 ml, is collected in a blood bank via venipuncture and placed into bag A, and then fractionated into its component parts using standard techniques into bags A, B and C. For example, bag A containing the blood sample is centrifuged. After centrifugation, the blood components are separated, e.g., using a blood component extractor manufactured by Baxter. The buffy coat containing leukocytes is placed into bag C, plasma is placed into bag B and erythrocytes remain in bag A. Thus, as a result of this process, bag A contains packed erythrocytes; bag B contains plasma; and bag C contains the buffy coat containing leukocytes (and possibly residual plasma and erythrocytes). Alternatively, the blood components can be separated from whole blood via apheresis techniques known in the art.

Bag A is then disconnected from the three-bag set. As illustrated in FIG. 2, bags B and C are then welded to custom made infusion bags 1-5 (Set-2) to form the system used to make the activated leukocyte suspension and then the ALCS. As described in these embodiments, bags 1-5 have volumes of 500 ml, 50 ml, 50 ml, 100 ml and 500 ml, respectively. As disclosed above, welding is performed with a sterile connecting device.

Bag 1, which is used for both first and second incubations of the leukocytes, contains 200 ml of sterile filtered air. If bag 1 is gas-permeable, there will be no need for air bags. Gas-permeable bags may also be treated or otherwise modified so that they become adhesive for leukocytes. For example, the bags may contain scaffolds such as adhesive beads and/or leukocyte agonists such as complement protein, interferon-alpha, interferon-gamma and interleukin-12. Leukocyte adhesion to the bag surface could be beneficial for their ability to release soluble agonists. The bags could be made from adhesive plastic or regular plastic treated in such a way as to become adhesive (corona discharge, liquid gas plasma, etc.), or coated with extracellular matrix proteins or chemically modified. The scaffolds may be in different shapes and in particular could be microbeads, biodegradable or not biodegradable. The scaffolds or beads may be biodegradable or not biodegradable, e.g., made of collagen or PLA, PGA (polylactic acid, polyglycolic acid) or similar synthetic polymers, hyaluronic acid, alginate or fibrin sealer. The beads could be synthetic hydrogel beads, gelatin beads, beads coated with adhesion receptors, activating stimuli or stimulating antibodies. The scaffolds or beads with adherent cells may be then centrifuged out together with all other cells. Also, the stimuli that otherwise are not desirable in the product will be eliminated together with scaffold or beads.

Bag 2 contains a solution (e.g., 20 ml of buffered sodium chloride solution (8.91% NaCl, USP), or any other physiologically acceptable solution containing inorganic ions, organic osmolytes such as sucrose, or some combination thereof, such as Lactated Ringer's (Hartmann's) solution), which serves to restore the leukocytes to isotonicity following hypo-osmotic shock. When the sodium chloride solution is added to 200 ml of distilled water (in bag 5), it becomes a 0.9% NaCl solution. Bag 3 contains 20 ml of sterile filtered air. Bag 4 contains a solution (e.g., about 60 ml of buffered calcium chloride solution (1.17% $CaCl_2$ dihydrate, USP), which acts to coagulate the plasma in bag B, and to facilitate separation into platelets and serum. Bag 5 contains about 200 ml water.

Figure 2A:
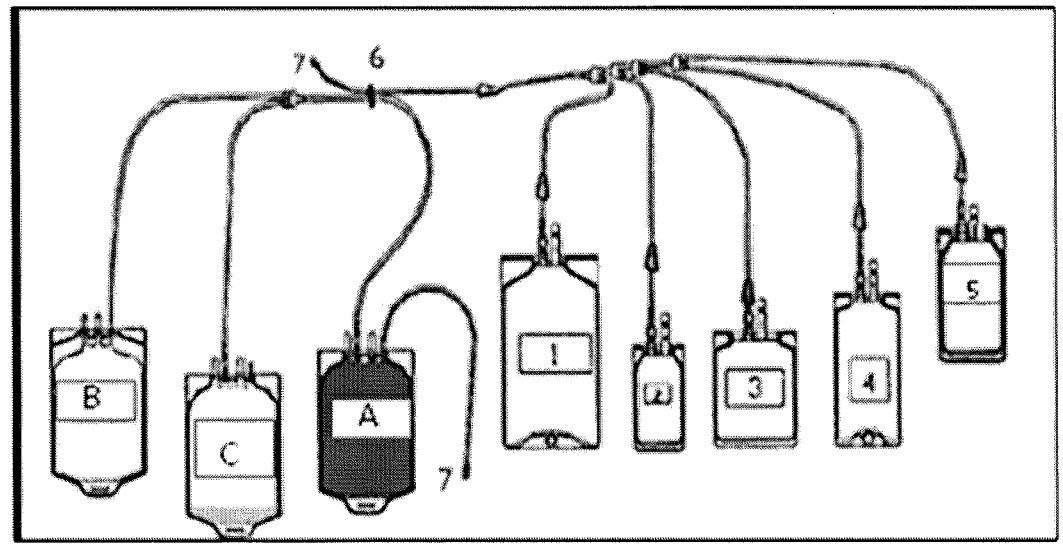
FIG. 2A schematically depicts a second portion of the representative system for producing ALC compositions of the present invention, which includes a 7-bag set after bag A with RBC is removed from the system and bags B and C from FIG. 1 are welded to bags 1-5 (Set-2)
Figure 2B:
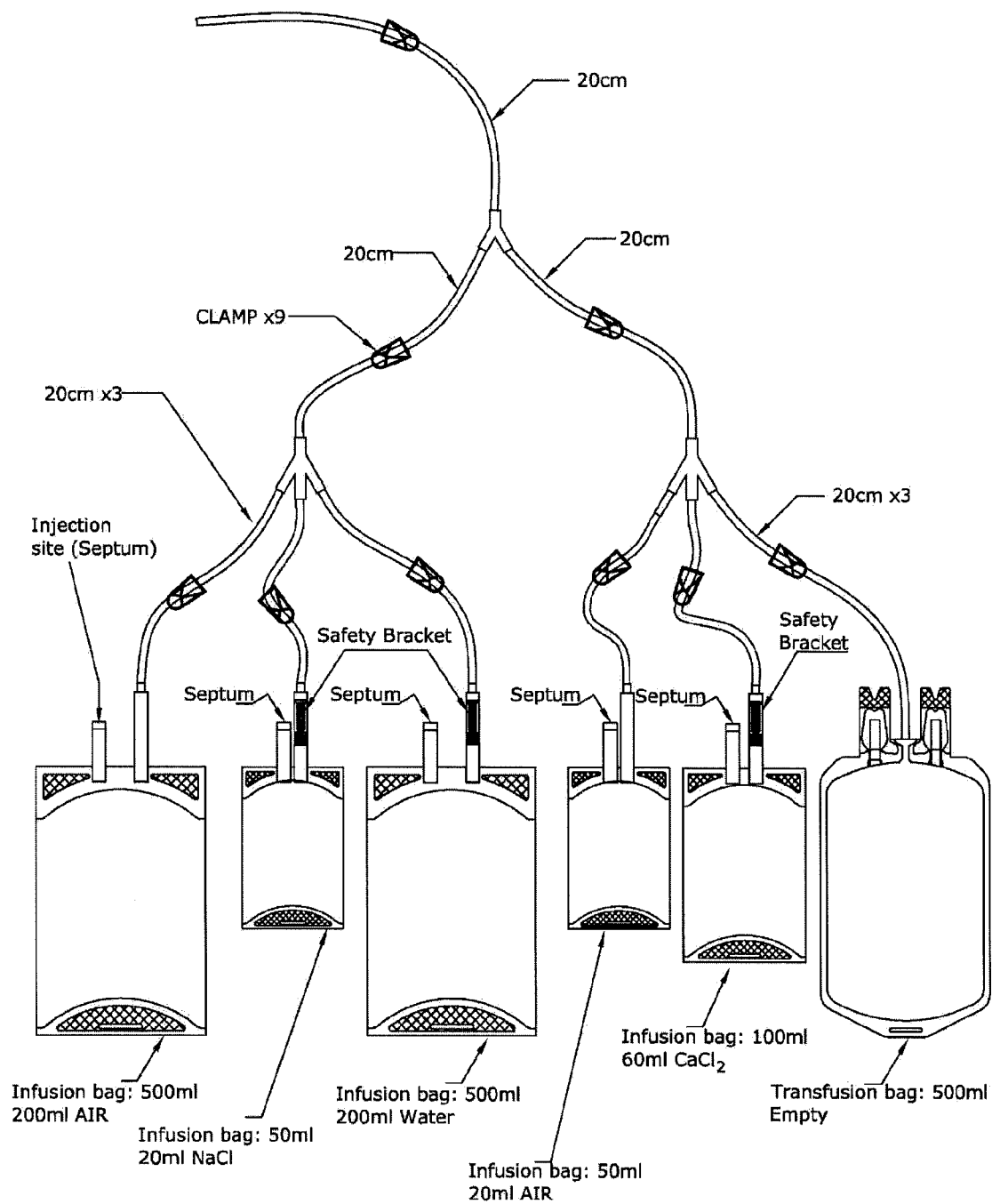
FIG. 2B shows a 6-bag set that may be used in lieu of bags 1-5 in FIG. 2A.

In an alternative embodiment, the 6-bag set illustrated in FIG. 2B may be used in place of bags 1-5 illustrated in FIG. 2A. The additional bag helps maintain sterility of the clean room production site. In this embodiment of the present method, after separation into buffy coat, plasma and RBC, leukocytes as previously described are transferred from bag C to a sterile bag 1 and the plasma is placed into the sixth bag which is also sterile, and then the 6 bag system is separated from the original triple bag set.

The set is packed as a single unit and sterilized using high pressure steam, which greatly reduces the risk of secondary infection to the patient.

The leukocytes are then transferred from bag C into bag 1 and incubated while the bag is maintained in a vertical or in a flat position and under activating conditions including time and temperature, to allow them to become activated.

For purposes of the present invention, in the various aspects and embodiments of the invention "leukocyte activation" is defined as a process involving at least one stage, by which the cells (leukocytes) undergo a transition from a quiescent to a functionally active state which is accompanied by synthesis of biologically active substances or translocation of pre-synthesized substances, e.g., cytokines such as IL-8, from the cytoplasm to the cellular membrane or their release into extracellular medium.

A "supernatant" is an extracellular medium which has been rendered substantially cell free, whether by centrifugation, sedimentation by gravity, filtration, or other methods of cell removal.

For purposes of the present invention, in the various aspects and embodiments of the invention, a "subtantially cell-free" supernatant is defined as a supernatant containing fewer than about $1 \times 10^6$ leukocytes per milliliter. In some embodiments, a substantially cell-free supernatant contains fewer than about $1 \times 10^5$, about $1 \times 10^4$, about $1 \times 10^3$, about $1 \times 10^2$, or about $1 \times 10^1$ leukocytes per milliliter. In some embodiments, a substantially cell-free supernatant is one in which leukocytes are undetectable.

Activation of leukocytes in vivo may involve migration of the cells closer to and along the blood vessel wall, which is mediated by P-selectin (and increased CD42b expression), increased adhesion of leukocytes to the endothelial wall, spreading and extravasation, which is mediated to a large degree by activated CD11b that interacts with endothelial ligands ICAM-1 and ICAM-2; migration to the focus of inflammation via interaction with extracellular matrix proteins (e.g., laminin) and functional responses to inflammatory stimuli such as respiratory burst, degranulation, phagocytosis and release of cytokines.

For purposes of the present invention, activation of the leukocytes is indicated by at least one, but often two or more, of the following several indicators. One indicator of leukocyte activation is increased expression of activated form of CD11b receptor on leukocyte populations including granulocytes, monocytes and lymphocytes, and/or lower expression levels of CD62L, a selectin adhesion receptor, which sheds off the leukocyte surface promoting firm adhesion of leukocytes to endothelial cells via CD11b. In some embodiments, leukocytes may also exhibit increased levels of CD69, a lymphocyte-specific activation marker, express platelet marker 42B (as a result of the interaction between activated granulocytes and monocytes with residual platelets in the buffy coat via p-selectin) and/or increased production of IL-8. Yet other indicia of leukocyte activation may include increased production of one or more of proteins or polypeptides, lipids, sugars, oxygen radicals and other biochemical moieties that function as adhesion molecules, cytokines in addition to IL-8, growth factors, enzymes, transcription factors and cell signaling receptors and mediators. Altered expression levels of any of these molecules is assessed from the standpoint of the leukocytes contained in a "fresh buffy coat" (as described herein), without being subjected to an incubation. Once the leukocytes are activated, they remain activated and as described herein, may achieve higher levels of activation, e.g., even greater expression levels of CD11b; greater or even greater expression levels of CD69, and even lower expression levels of CD62L. In addition, once activated, leukocytes may further increase their ability to produce cytokines, such as IL-8, IL-6, TNF-alpha and VEGF. Other examples of cell surface markers and secreted soluble factors indicating leukocyte activation are provided in the Examples. Thus, an "activated leukocyte composition" is a composition comprising leukocytes that exhibit at least one of the indicia of activation. In some embodiments, the activated leukocytes further comprise platelets.

In some embodiments, the leukocytes are incubated simply by allowing them to stand at room temperature. For purposes of the present invention, room temperature refers to a temperature in the range of about 12° C. to about 28° C., and in some embodiments from about 16° C. to about 25° C., from about 18-25° C. and from about 20-25° C. The time period of incubation may vary depending upon the temperature and generally varies from about 30 minutes to about 24 hours. The incubation time needed to activate the leukocytes will be roughly inversely proportional to the temperature at which the incubation is conducted. Thus, incubation times will be lower at increased temperatures. For example, in embodiments where leukocytes are allowed to stand at room temperature, the incubation time generally ranges from about 90 minutes, and upwards of 2, 3, 4, 5, 6, 7, 8, 9, 10, 11, 12, 13, 14, 15, 16, 17, 18, 19, 20, 21, 22, 23 or upwards of 24 hours (and subranges thereof which include, for example a minimum time of anywhere from 90 minutes, 2 hrs, 3 hrs, 4 hrs, 5 hrs, 6 hrs, 7 hrs, 8 hrs, 9 hrs, 10 hrs, 1 hrs, 12 hrs, 13 hrs, 14 hrs, 15 hrs, 16 hrs or higher). In preferred embodiments, the incubation time ranges from about 3, 4, 5, 6, 7 or 8 hours to about 20 hours. In a more preferred embodiment, incubation of the leukocytes occurs at about 18° C. to about 24° C. for about 8 hours to about 12 hours. In other embodiments, incubation of the leukocytes involves exposing them to heat, e.g., at a temperature above room temperature and up to about 37° C. The time period for incubation at elevated temperatures generally ranges anywhere from 30, 45, 60, or 90 min to about 2, 3, 4, 5, 6, 7, 8, 9, 10, 11 or 12 hours (and even upwards, in hour increments) to about 24 hours (and subranges thereof which include, for example, a minimum time of anywhere from 30, 45, 60 or 90 mins, 2 hrs, 3 hrs, 4 hrs, 5 hrs, 6, hrs, etc.).

After incubation, the leukocyte suspension is generally subjected to hypo-osmotic shock. In preferred embodiments, hypo-osmotic shock is performed immediately (i.e., upon completion of the preceding step without any intervening step or unnecessary delay, typically less than 2 minutes). For example, in the system described in the Figures, the hypo-osmotic shock may be initiated by transferring the distilled water from bag 5 to bag 1 containing the leukocytes. The hypo-osmotic shock treatment is typically conducted for about 25-45 seconds. Lesser times within this range are preferred, as it is believed that fewer CD4+ T cells are lost. CD4+ T cells are known to produce various cytokines (e.g. IFN gamma, IL-2, IL-4, IL-17), which might be beneficial for wound healing. Following this step, and preferably immediately thereafter, isotonicity is restored to the leukocytes. Referring again to the system described in the Figures as an exemplary embodiment, this is accomplished by transferring the sodium chloride solution from bag 2 to bag 1. The ratio of the volume of sodium chloride solution to cell suspension in water is generally about 1:10.

Following the treatment that restores isotonicity, the entire system is centrifuged. This process removes water and salt solution added in the course of the two prior steps, and prevents exposure of the leukocytes to hemolysate (of the erythrocytes). As a result of the centrifugation, the leukocytes form a pellet. After centrifugation, the supernatant from bag 1 is transferred into bag C, and the leukocyte pellet formed in bag 1 as a result of the centrifugation is re-suspended in serum or other medium used for conditioning by leukocytes.

In one embodiment, serum is obtained by a sequence of separate steps, which may be conducted concurrently with the first leukocyte incubation, which entails contacting plasma with a coagulant such as $CaCl_2$. This process results in formation of a blood clot of predominately fibrin strands and platelet aggregates. As a result of this treatment, the resulting serum has a residual platelet level that generally ranges from about 0 to about $0.2 \times 10^3$ per µL. Thus, in this embodiment, $CaCl_2$ from bag 4 is transferred to bag B. Bag B, which now contains a composition of plasma and $CaCl_2$, is typically allowed to coagulate at a temperature of about 37° C. Although in this embodiment the plasma remains in contact with the coagulating agent for substantially the same period of time the leukocytes are incubated for purposes of activation, the plasma may remain in contact with the coagulation agent for a different and substantially shorter time, e.g., about 90 minutes to about 24 hours.

Leukocyte pellets in bag 1 obtained after restoring isotonicity and centrifugation are mixed with about 20 ml to about 200 ml or more of serum from bag B (which may be obtained from the same or a different blood sample as the leukocytes) to form an incubation composition comprising in this case serum.

Although activated leukocytes prepared using exemplary bag systems have been described, any composition prepared by incubating leukocytes for a period of time so that the leukocytes transition from a quiescent to a functionally active state, subjecting the leukocytes to a hypo-osmotic shock, and restoring the isotonicity of the leukocyte composition can be used to provide activated leukocytes for use in preparing the activated leukocyte conditioned supernatant.

In addition, although serum (particularly human serum) is often used in the incubation composition, other media may be used as well so long as it is a physiologic medium that supports release of cytokines, growth factors, and/or other soluble components from the activated leukocytes. For example, plasma may be used instead of serum. Other incubation medium that may also be used include culture medium, or saline or buffered saline solutions with possible addition of sugars and other components essential for cell viability and function such as amino acids (e.g. Lactated Ringer's solution, Acetated Ringer's solution, Hank's balanced salt solution (HBSS), Earle's balanced salt solution (EBSS), Standard saline citrate (SSC), HEPES-buffered saline (HBS), Gey's balanced salt solution (GBSS)). Saline solutions and culture medium could be supplemented with human serum or clinical grade animal serum, or serum substitutes. The incubation composition may alternatively, or in addition, contain serum proteins such as human or bovine albumin, gamma-globulin, transferrin or other proteins from different tissues, plant proteins, or plant extracts. Further, an agonist(s) such as interferon-gamma may be added to the incubation composition to boost release of soluble agonists from the cells.

The incubation composition is incubated under conditions of time and temperature to condition the supernatant, thus producing the activated leukocyte-conditioned supernatant. These conditions include a temperature of about room temperature (i.e., in the range of about 12° C. to about 28° C., and in some embodiments from about 16° C. to about 25° C., from about 18-25° C. and from about 20-25° C.) to about 37° C. The incubation time generally ranges anywhere from 30, 45, 60, or 90 min to about 2, 3, 4, 5, 6, 7, 8, 9, 10, 11, 12, 18, 24, 36, 48, 60 to about 72 hours, or even longer. In some embodiments, the composition is incubated at room temperature from about 1 to about 48 hours, for example, at about 18° C. to about 24° C. for about 8 hours to about 18 hours, or for about 1 hour, about 24 hours, or about 48 hours. In other embodiments, the composition is incubated at about 37° C. for about 1 to about 5 hours, or for about 30 min, about 60 min, or about 5 hours. As a result, the supernatant becomes conditioned, in that the leukocytes secrete into the supernatant numerous cytokines, growth factors and other soluble biologically active molecules, which at the end of the process, are present in the supernatant in supra-normal concentrations (i.e., higher than in serum isolated from a normal, non-pathogenic donors and, in the case of autologous serum, higher than in the serum of the patient with the wound). To stimulate production and secretion of cytokines, an agonist such as interferon-gamma may be added to the incubation composition. As shown in the working examples, as a result of the second incubation, the leukocytes achieve higher levels of activation, e.g., even greater expression levels of CD11b and particularly CD69, even lower expression levels of CD62L, and increased production of IL-8 and other cytokines and growth factors.

Following this second incubation, the leukocytes are substantially removed, for example, by centrifugation, sedimentation by gravity force, filtration, or other methods of cell removal. In some embodiments, leukocytes are completely removed to provide a cell-free ALCS. For example, in those embodiments utilizing the bag system, the entire bag system is centrifuged again (to separate leukocyte pellet in bag 1 from ALCS). Alternatively, bag 1 with leukocytes and conditioned serum is separated from the system before centrifugation, a new empty bag (not shown in FIG. 2) is welded, that is, joined, to bag 1, and then these two bags are centrifuged to separate the leukocyte pellet from ALCS. After centrifugation, the liquid part of bag 1 is transferred to either the remaining empty bag in the system or to a new bag.

In those embodiments in which the leukocytes are removed by centrifugation, centrifugation forces generally range between 300 g-10,000 g and centrifugation times between 5 min-60 min. In those embodiments in which it is desirable to reduce or eliminate residual platelets, g-forces above 1000 g are used so that platelets will also pellet. Higher speeds (40,000 g) can be used in those embodiments in which it is desirable to reduce or eliminate residual erythrocytes, RBC remnants, and other debris.

According to one aspect of the invention, an ALCS has a concentration of at least one cytokine(s), growth factor(s), or soluble mediator chosen from IL-8, PDGF, Ang-1, VEGF, IL-6, TNFalpha, or IL-1 beta that is at least about 1.25, 1.5, 2, 3, 4, 5, 6, 7, 8, 9, 10 or more times the concentration of that same cytokine, growth factor, or soluble mediator in the same medium used to prepare the incubation composition that resulted in that ALCS, but prior to contact of the medium with an activated leukocyte composition. For example, in some embodiments the ALCS has a concentration of at least one cytokine(s), growth factor(s), or soluble mediator chosen from IL-8, PDGF, Ang-1, VEGF, IL-6, TNFalpha, IL-1 beta, or combinations or subcombinations thereof, that is at least about 1.25, 1.5, 2, 3, 4, 5, 6, 7, 8, 9, 10 or more times the level of IL-8, PDGF, Ang-1, VEGF, IL-6, TNFalpha, or IL-1 beta of the non-conditioned serum described in Table 7, either including or not including the standard deviation. In some embodiments, the higher concentration is relative to at least IL-8, at least PDGF, at least Ang-1, at least VEGF, at least IL-6, at least TNFalpha, or at least IL-1 beta. In other embodiments, the higher concentration is relative to at least two of, at least three of, at least four of, at least five of, at least six of, or all seven of IL-8, PDGF, Ang-1, VEGF, IL-6, TNFalpha, or IL-1 beta.

Subsequent to this procedure, the substantially cell-free ALCS may be frozen, or lyophilized or freeze-dried. Additives such as preservatives (e.g., antioxidants, sugars such as trehalose, sodium chloride) may be beneficial from the standpoint of maintaining activity of the cytokines and growth factors. The leukocyte pellet may be stored as well, thus allowing for reuse to condition other media to provide additional ALCSs.

In those embodiments utilizing serum and/or plasma, it should be noted that although the serum and/or plasma for use in various aspects of the invention may be prepared at the same time as the activated leukocyte composition (whether from the same or a different blood sample), in alternate embodiments the serum and/or plasma is prepared independently of the activated leukocyte composition. For example, serum and/or plasma may be obtained from a commercial or non-profit supplier of blood products. The serum and/or plasma may be recently obtained from one or more donors, or it may have been stored for a period of time, and may be stored frozen. Further, since blood samples used to prepare the serum and/or plasma need not be the same as used to prepare the activated leukocytes (whether or not they are from the same donor), their preparation need not occur at the same physical location or at the same time as preparation of the activate leukocyte composition.

In those embodiments in which the ALCS is stored prior to use, it may be stored at room temperature, refrigerated, or frozen. In those embodiments in which the ALCS is stored at room temperature, it has a shelf life ranging up to about 5 days following its production, for example about 12, 24, 48, 72 or more hours following its production.

In those embodiments in which the ALCS is stored refrigerated, it has a shelf life that is at least about 7 days or more, for example, at least about 1, 2, 3, 4, 5, 6, 7, or 8 weeks, or from about 1-2 weeks, about 1-3 weeks, about 1-4 weeks, about 1-5 weeks, about 1-6 weeks, about 1-7 weeks, or about 1-8 weeks.

In those embodiments in which the ALCS is stored frozen, it may be stored frozen and then thawed when needed. In some embodiments, the frozen ALCS has a shelf life that is at least about 1 week to one month, or at least about 1, 2, 3, 4, 5, 6, 7, 8, 9, 10, or 11 months up to one year, or at least about 1 year, at least about 2 years, or at least about 3 years.

In other embodiments, the ALCS composition may be prepared from smaller volumes of blood samples, with commensurate decreases in volumes of all solutions and use of smaller bags. Furthermore, use of these different size bags and different volumes of serum yield ALCS with different concentration of soluble substances. Even in these embodiments, allogeneic or autologous blood samples may be used as starting materials. Use of smaller volumes provides the clinician with the ability to perform the blood collection autonomously, without using an external blood bank, such as in emergency situations in treating patients with otherwise healthy immune systems but suffering from some type of traumatic wound (e.g., battlefield and combat conditions). In these embodiments, testing for transmittable diseases and antigens may be dispensed with. However in such cases, patients with refractory wounds are not clinically acceptable blood donors for effective ALCS preparation. When this situation arises, ALCS will be produced from allogeneic donors by the means described herein.

Patients suffering from wounds can be physiologically compromised or otherwise healthy. For example, due to already impaired metabolic systems, diabetics and other medically compromised patients are candidates for ALCS derived from heterologous blood, as their own leukocytes may not be optimal for the procedure. However, otherwise healthy patients, as in the example of trauma patients, are also good candidates for ALCS compositions of the present invention.

The present invention is useful in treating and promoting healing of any type of wound. In some embodiments, the ALCS, for example, a substantially cell-free ALCS, is administered to the wound as the sole active wound healing agent. In other embodiments, it is used in combination with other treatment modalities. The ease of application, e.g., with a standard syringe or similar application device, makes the inventive ALCS compositions safe and easy to use.

Wounds amenable to treatment with the invention are typically in the form of burns, punctures, cuts or tears of the living tissues. Wounds of the skin can penetrate the epidermis, dermis or in the case of full-thickness wounds, the subcutaneous tissue. Thus, representative types of wounds amenable to treatment with the compositions and methods of the present invention include burns (e.g., caused by exposure to fire or an agent that is highly caustic to skin), ulcers (e.g., decubitus ulcers or any other pressure ulcers, venous ulcers, and diabetic ulcers), tendonitis, deep sternal wounds, e.g., following open heart surgery; surgical wounds to the great saphenous vein after coronary revascularization and harvesting of the great saphenous vein; and post-operative wounds following abdominal and any other types of surgery. Other wounds are those which result from trauma such as incurred during combat or other violent activity, including wounds caused by gun shots, knives, or any other object able to cause a cut or tear in the skin. Wounds of the oral cavity (e.g., teeth), as well as wounds that arise as a side-effect of medication or as a symptom of various pathologies (e.g., sores associated with Kaposi's Sarcoma), as well as internal wounds (e.g. ruptures of muscle tissue such as anal fissures), and wounds or lesions to the gastrointestinal tract, such as ulcers in the stomach or intestines) may also be amenable to treatment with the present invention.

The ALCS may also be used to treat any wounds exacerbated by vascular insufficiency. Vascular insufficiency, for purposes of the present invention, refers to inadequate blood circulation resulting in insufficient perfusion to the afflicted areas. Such insufficiency can be caused by trauma (e.g. damage to the vasculature adjacent to a skeletal fracture), or various pathologies (e.g. diabetes and atherosclerosis). In either instance, whether trauma or disease induced, vascular insufficiency decreases the likelihood of effective wound healing. The ALCS may be useful in improving wound healing outcomes in these patients and should be administered according to the methods described herein. Additionally, treatment algorithms should not be limited by the severity or type of wound, or the extent of vascular insufficiency. ALCS may be more efficacious in patients presenting with the most severe wounds and vascular insufficiency.

The activated leukocyte-conditioned supernatant is particularly useful in treating diabetic foot ulcers and decubitus ulcers. Decubitus ulcers are chronic pressure ulcers of the skin and underlying tissues caused by prolonged pressure and impeded blood flow on the body surface of bedridden patients (Berlowitz, 2007). Decubitus ulcers cause morbidity and mortality in elderly people. At least 48% of stage IV pressure ulcers remain unhealed after one year of treatment. (Girouard, 2008). Patients suffering from decubiti also commonly have co-morbid pathologies such as diabetes and hypertension. These pathologies further complicate the successful treatment of decubiti.

In other aspects, the invention is directed to a method of inhibiting the onset of infection in a wound, comprising administering to the wound a composition of the invention. In one embodiment, the wound is caused by trauma. In another embodiment, the wound is caused by surgery.

In those aspects involving methods of treating a wound, the wound may also be treated by administering to the wound an article of manufacture comprising a composition of the invention.

In general, application of the activated leukocyte-conditioned serum is accomplished by means of one or more injections of the ALCS directly into the wound or the tissue surrounding the wound. The ALCS may be applied directly into an open wound. The entire sample in the syringe can be deployed and the clinician can choose to administer additional ALCS if it is determined to be necessary based on clinical parameters.

The ALCS may be injected into the wound in various locations. In one embodiment, injection occurs about every one centimeter to about every three centimeters for the entire length of the wound. At each injection site, 0.1-0.3 ml of ALCS is injected. In other embodiments, the entire syringe can be injected at one time into a single site within the wound.

For injection into the wound, it is preferred to use a Luer-Lock syringe or any other commercially available syringe that has a locking mechanism between the syringe and the needle. The biological space of a wound, particularly a pressure wound, is often limited. When injecting into a wound, there is a risk of pressure causing the syringe to separate from the needle. Using a locking syringe eliminates this risk. If the 18G or larger needle is used for aspiration, it is exchanged with a needle ranging in size from 22-35G for injection into a wound.

When injection into the wound tissue is not possible, the ALCS can be applied directly into the cavity of the wound.

Application in this method can be performed using direct application with a syringe or tubing.

The ALCS may be applied to or around the wound site with the aid of a dressing. Dry dressings include gauze and bandages, non-adhesive meshes, membranes and foils, foams, and tissue adhesives. Moisture-keeping barrier dressings include pastes, creams and ointments, nonpermeable or semipermeable membranes or foils, hydrocolloids, hydrogels, and combination products. Bioactive dressings include antimicrobial dressings, interactive dressings, single-component biologic dressings, and combination products (e.g., ointments, gels, fibrin sealant, growth and angiogenic factors (e.g., PDGF, VEGF, collagen). In some embodiments, the wound is packed with sterile gauze soaked in the ALCS. The dressing, e.g., such as sterile gauze pads, may be saturated with compositions such as Lactated Ringer's (Hartmann's) solution, alginate-containing dressing, polyurethane dressing or carboxymethylcellulose dressing, which is applied to cover the wound, followed by application of dry dressing. If the subject wound is highly infected, then silver dressings such as Silverton can be applied. The choice of post-injection dressing is based on the determination of the clinician. Commercial availability, history of past clinical success, and patient tolerance are all factors to be considered in the selection of a wound dressing. The dressing may be removed periodically, e.g., typically after about 24 hours, in order to irrigate the wound e.g., with sterile water and soap.

In another embodiment, the ALCS is combined with a physiologically inert and/or resorbable matrix or scaffold prior to administration. The matrix or scaffold may be formed from any material suitable for implantation into a person. For example, the matrix or scaffold may comprise any biocompatible material including collagen, hyaluronic acid, or gelatin, foam, or combinations thereof. The collagen may be obtained from any source, including collagen prepared from human tissue or the tissue of other collagen-producing mammals. The combination of the ALCS and matrix/scaffold material may form a foam, a gel or putty that is administered to a person by means of a press fit, or by injection. This allows for a sustained delivery of the ALCS into the site which benefits the patient. The foam may comprise a fibrin sealant. In some embodiments, the mixture of the ALCS and matrix/scaffold material is prepared commercially and provided to a health-care provider pre-mixed. In other embodiments, the health care provider mixes the ALCS and the matrix/scaffold prior to administration to a person.

The ALCS may be applied to the wound once or more than once, e.g., after 4 weeks, once a clinician determines whether another application is necessary. Factors that may be taken into account include increased wound dimensions (width, length and depth), suppuration, pyrexia or any other sign or symptom indicating a recalcitrant wound infection such that re-treatment is warranted. In addition to re-treatment, referral for surgical debridement may be indicated at any point the clinician deems appropriate.

The ALCS may be used in conjunction with any other conventional wound treatment, such as warming (therapeutic heat), electrical stimulation, magnetism, laser phototherapy, cycloidal vibration therapy and ultrasound. It also can be used with biological therapy such as larva therapy, skin substitutes, cultured keratinocytes (Epicel, Genzyme biosurgery), human dermal replacement (Dermagraft, Smith and Nephew Inc.), cadaver derived processed dermis (Alloderm, Life Cell Corporation), Bilayered Skin Equivalent (Apligraf, Organogenesis Inc.), TransCyte (Smith and Nephew Inc.), Growth Factors (PDGF is currently the only growth factor licensed for topical use), and fibrin sealant. In some embodiments, the ALCS is used in conjunction with VAC, which is a commercially available wound therapy manufactured by KCI. VAC promotes wound healing by applying negative pressure to a wound. In these embodiments, ALCS is preferably applied to a wound prior to VAC therapy. In yet other embodiments, the ALCS is used in conjunction with hyperbaric therapy (Thackham, 2008). For example, the ALCS can be applied to a wound just prior to a patient receiving hyperbaric therapy. The ALCS may also be used in conjunction with low-energy shock wave therapy (e.g., impulses of about 0.1 mJ/mm$^2$; 5 Hz) per centimeter of wound length). See, e.g., Dumfarth, et al., Ann. Thorac. Surg. 86:1909-13 (2008).

After treatment, the wounds may be evaluated for length, width and height measurements. Typically, a wound is considered healed when all measurements of these parameters are negligible. The ALCS may also provide an analgesic effect.

Aspect(s) of the present invention will now be described in accordance with the following non-limiting examples.

Example 1

Analysis of Cellular Activation

An activated leukocyte composition made in accordance with a preferred embodiment of the present invention for conditioning of serum, was characterized by the analysis of cell surface markers, namely CD11b, CD62L and CD69 on various leukocyte populations (granulocytes, monocytes and lymphocytes).

CD11b is an adhesion receptor for ICAM-1 (CD54) and other ligands. It is expressed mostly on granulocytes and monocytes/macrophages but at lower levels also on lymphocytes. Expression of CD11b on cell surface increases upon leukocyte activation. In addition CD11b changes conformation. Activated form of CD11b is recognized by the antibody CBRM1/5. Non-activated form of CD11b is recognized by a different antibody (D12).

CD62L is an adhesion receptor from a selectin family. It is constitutively expressed on all classes of leukocytes including granulocytes, monocytes and lymphocytes. Upon activation, leukocytes rapidly shed off CD62L from their surface.

CD69 is a lymphocyte activation antigen. CD69 expression increases very early on lymphocyte surface upon activation.

Leukocytes were sampled at three time points: immediately prior to the beginning of the production process (fresh buffy coat (FBC); right after the first incubation (incubated buffy coat (IBC)); and at the end of the activation process (EAP), meaning after hypo-osmotic shock, followed by a second, 90 min incubation with serum at 37° C. At each time point, leukocytes were labeled with specific monoclonal antibodies against corresponding activation markers and then analyzed by flow cytometry.

For antibody staining, cells from each time point were washed with PBS/0.02% Sodium Azide, and resuspended in FACS staining solution (PBS, 2% Normal Mouse Serum; 0.02% Sodium Azide) at $0.5 \times 10^6/100\,\mu l$. Aliquots of 100 µl of cell suspension were incubated with appropriate monoclonal antibodies for 30 min. at +4° C. in the dark. After incubation, the cells were treated with erythrocyte lysis buffer, washed, re-suspended in PBS and analyzed on FACSCalibur flow cytometer (Becton Dickinson). Anti-CD11b and anti-CD62L antibodies were conjugated to phycoerythrin (PE), and CD69 antibody was conjugated to fluorescein isothiocyanate (FITC). In order to better distinguish between leukocyte populations, cells labeled with CD11b were also double-labeled with the antibody against a monocyte marker CD14 conjugated to allophycocyanin (APC), and cells labeled with and CD62L antibodies were also double-labeled with granulocyte marker CD15-APC. In order to identify T and B lymphocytes, cells stained with CD69 antibody were also double-stained with anti-CD3-APC and anti-CD19-APC antibodies. Cells stained with irrelevant but isotype-matching antibodies (together with anti-CD14 or anti-CD15, or anti-CD3/CD19 antibodies) under the same conditions were used as negative controls. Monocytes were determined as CD14 brightly positive cells and granulocytes were identified as CD14 dimly positive cells or CD15 brightly positive cells with high side light scattering properties (SSC). T Lymphocytes were determined as CD3 positive cells and B lymphocytes were determined as CD19 positive cells. The results of 4-6 such experiments are summarized in Tables 1, 2 and 3. The data are presented as Mean Fluorescence Intensity of stained cells plus/minus StDev.

The data shown in Table 1 demonstrate that the level of expression of CD11b recognized by both general (D12) and anti-activated form (CBRM1/5) antibodies significantly increased at the end of the activation process (EAP) on all leukocyte populations compared to Fresh Buffy Coat (FBC). Upregulation of activated form of CD11b was more pronounced.

As shown in Table 3, the upregulation of CD11b and downregulation of CD62L were consistent with the expression of a specific lymphocyte activation marker CD69, which increased from practically no expression to moderate but significant levels.

Example 2

Analysis of Secretion of Cytokines by Activated Leukocytes During Incubation in Serum An activated leukocyte composition containing $10 \times 10^6$ cells was centrifuged, and the cell pellet resuspended in 5 ml of serum in accordance with a preferred embodiment of the present invention. The concentration of IL-8 and other cytokines was measured at various time points of incubation at 37° C. using optimized ELISA plates from R & D Systems. Concentrations of cytokines (pg/ml) in serum used for leukocyte resuspension (without leukocytes) were measured in parallel and subtracted from values produced in the presence of activated leukocytes. The results of five experiments for IL-8 are summarized as Mean±SD in Table 4. The results of additional experiments for various cytokines and growth factors (GF) are summarized in Table 5 (n>10).

TABLE 1

Expression of CD11b on leukocyte populations indicating leukocyte activation.

| | CD 11b (D12 antibody) Mean Fluorescence | | | | CD 11b activated form (CBRM 1/15 antibody) Mean Fluorescence | | | |
|---|---|---|---|---|---|---|---|---|
| samples | GR | Mono | T cells | B cells | GR | Mono | T cells | B cells |
| FBC | 635 ± 282 | 657 ± 104 | 1.6 ± 1.1 | 6.7 ± 3.3 | 22 ± 13 | 6 ± 4 | 0 | 0.2 ± 0.1 |
| IBC | 1099 ± 85 | 589 ± 12 | 1.6 ± 1.2 | 8.6 ± 5.8 | 37 ± 6 | 4 ± 1 | 0 ± 0.1 | 0.3 ± 0.2 |
| EAP | 1100 ± 144 | 663 ± 48 | 26.9 ± 21.6 | 14.3 ± 2.2 | 225 ± 85 | 22 ± 8 | 0.6 ± 0.3 | 1.5 ± 0.7 |

TABLE 2

Expression of CD62L on leukocyte populations indicating leukocyte activation.

| | CD 62L Mean Fluorescence | | | |
|---|---|---|---|---|
| samples | GR | Mono | T cells | B cells |
| FBC | 583 ± 428 | 205 ± 187 | 256 ± 123 | 577 ± 165 |
| IBC | 34 ± 25 | 14 ± 8 | 86 ± 54 | 32 ± 19 |
| EAP | 19 ± 10 | 16 ± 4 | 13 ± 6 | 24 ± 13 |

TABLE 3

Expression of CD69 on T and B lymphocytes indicating their activation.

| | CD69 Mean Fluorescence | |
|---|---|---|
| samples | T cells | B cells |
| FBC | 0.2 ± 0.2 | 0.2 ± 0.1 |
| IBC | 0.6 ± 0.4 | 0.6 ± 0.4 |
| EAP | 6.3 ± 4.5 | 8.2 ± 3.4 |

Comparison of CD62L expression at different stages of the production process demonstrated that it drastically and significantly decreased on all leukocyte populations already at the stage of Incubated Buffy Coat (IBC). At the end of activation process (EAP), CD62L levels were negligible (Table 2).

TABLE 4

Concentrations of IL-8 (pg/ml) released into serum by activated leukocytes.

| Time of incubation of ALC with serum | | |
|---|---|---|
| 0.5 hour | 1 hour | 5 hours |
| 1115 ± 519 | 2581 ± 865 | 12461 ± 9491 |

TABLE 5

Concentrations of cytokines and growth factors (pg/ml) released into serum by activated leukocytes

| Cytokine/GF | Time of incubation in serum | |
|---|---|---|
| pg/mL | 3 hours | 5 hours |
| IL-8 | 2892 ± 2014 | 7151 ± 3914 |
| PDGF-BB | ND | 484 ± 27 |
| Ang-1 | 1132 ± 2209 | ND |
| VEGF | 44.2 ± 30 | 66.5 ± 34.6 |
| IL-6 | 17.2 ± 18.8 | 50.6 ± 48.3 |
| TNFalpha | 27.3 ± 19.8 | 30.4 ± 18.4 |
| IL-1beta | 4.9 ± 4.5 | 16.0 ± 13.8 |

The data presented in Table 4 and Table 5 demonstrate the ability of activated leukocytes to support sustained release of IL-8 and other cytokines and growth factors related to wound healing into supernatant for at least 5 hours.

Example 3

Comparison of the Ability of Leukocytes Sampled from Raw Material (Fresh Buffy Coat) and from Intermediate and End Stages of the Production Process to Release Cytokines and Growth Factors Leukocytes were sampled at three time points: immediately prior to the beginning of the production process (fresh buffy coat (FBC)); right after the first incubation (incubated buffy coat (IBC)); and at the end of the activation process (EAP), meaning after hypo-osmotic shock, followed by 90 min incubation with serum at 37° C. At each time point, leukocyte composition containing $10\times10^6$ cells was centrifuged and the cell pellet was resuspended in 5 ml of culture medium (RPMI) or original medium corresponding to each sample (plasma for fresh buffy coat, and serum for the incubated buffy coat and final product) in accordance with a preferred embodiment of the present invention. Leukocytes from each sample were incubated for 1 hour in RPMI and for 5 hours in plasma/serum at 37° C., and the concentration of various cytokines released during these time periods was measured using optimized ELISA plates from R & D Systems. While RPMI did not contain any cytokines, concentrations of cytokines (pg/ml) in corresponding plasma or serum used for leukocyte resuspension (without leukocytes) were measured in parallel and subtracted from values produced in the presence of activated leukocytes. The results summarized as Mean±SD (n=3-6) in Table 6.

TABLE 6

Comparison of cytokine and growth factor release by leukocytes sampled at different stages of the production process.

| Cytokine/GF | FBC | | IBC | | EAP | |
|---|---|---|---|---|---|---|
| pg/mL | RPMI | plasma | RPMI | serum | RPMI | serum |
| IL-8 | 80 ± 110 | 112 ± 42 | 434 ± 290 | 591 ± 434 | 1007 ± 1017 | 2232 ± 1153 |
| VEGF | 43 ± 22 | ND | 59 ± 23 | 59 ± 38 | 88 ± 53 | 107 ± 38 |
| IL-6 | 1.9 ± 3.0 | 0.1 ± 0.1 | 1.0 ± 1.6 | 9.3 ± 9.7 | 7.9 ± 14.4 | 157 ± 108 |
| TNFalpha | 0.0 | ND | 5.6 ± 9.5 | 18.9 ± 8.4 | 38 ± 50 | 76.8 ± 25.7 |

Data presented in Table 6 demonstrate that while leukocytes of the raw material (buffy coat) had low ability to release cytokines, cytokine release from leukocytes increased during the production process and was maximal at the end of production. When activated leukocytes at the end of production were resuspended in serum in accordance with a preferred embodiment of the present invention, cytokine release was 2-3 fold higher compared to release in RPMI.

Example 4

Analysis of Cytokine Content in the Final Product

Concentration of various cytokines and growth factors related to wound healing was measured in the liquid part of the final product (after the cells were pelleted by centrifugation) after incubation for 1 hour, 24 hours and 48 hours with activated leukocytes at RT. The assays were performed using optimized ELISA plates from eBioscience. The results are summarized as Mean±SD (n>10) in Table 7.

TABLE 7

Cytokine content at various time after the end of production

| Cytokine/GF | Time at RT (hours) | | | non-conditioned |
|---|---|---|---|---|
| pg/mL | 1 | 24 | 48 | serum |
| IL-8 | 3802 ± 3561 | 18648 ± 12211 | 28246 ± 507 | 711 ± 611 |
| TGFbeta-1 | 6475 ± 3627 | ND | ND | 4560 ± 1875 |
| PDGF-BB | 2275 ± 122 | 2271 ± 18 | ND | 1595 ± 82 |
| Ang-1 | 21660 ± 6571 | ND | ND | 22645 ± 6401 |
| VEGF | 266 ± 180 | 384 ± 204 | 226 ± 57 | 161 ± 151 |
| IL-6 | 7.4 ± 10.6 | 63.4 ± 61.1 | 74.5 ± 0.0 | 3.7 ± 3.6 |
| TNFalpha | 11.2 ± 10.1 | 16.2 ± 11.8 | 23.5 ± 6.4 | 10.4 ± 6.3 |
| IL-1beta | 7.5 ± 8.3 | 18.6 ± 14.7 | 26.4 ± 7.7 | 1.9 ± 2.2 |

The data shown in Table 7 demonstrate that at the end of production ALCS contains significant amount of relevant cytokines and growth factors. The cytokine concentrations increased when time of pre-incubation of activated leukocytes with serum in accordance with a preferred embodiment of the present invention was prolonged. Content of respective cytokines and growth factors (except Ang-1) in serum used prior to being conditioned by activated leukocytes was significantly lower by 2-3 fold.

LIST OF PUBLICATIONS CITED IN APPLICATION

Parkin, et al., *An Overview of the Immune System*. Lancet. 2001; 357:1777-1789.

A Moretta, et al., *Human NK Cells: From HLA Class I-Specific Killer Ig-like Receptors to the Therapy of Acute Leukemias*. Immunol. Rev. 2008 August; 224:58-69.

J. Li, et al., *Pathophysiology of Acute Wound Healing*. Clinical Dermatol. 2007 January-February; 25(1):9-18.

G. Broughton 2nd, et al., Wound Healing: An Overview. Plast Reconstr Surg. 2006 June; 117 (7 Suppl): 1e-S-32e-S.

A K Tsirogianni, et al., *Wound Healing: Immunological Aspects*. Injury. 2006 April; 37 Suppl 1:S5-12. Epub 2006.

A J Singer, et al., *Cutaneous Wound Healing*. New Eng. J. Med. 1999; 341(10):738-46.

P. Martin, *Wound Healing—Aiming For Perfect Skin Regeneration*. Science 1997; 276(5309):75-81.

A D Agaiby, et al., *Immuno-Inflammatory Cell Dynamics During Cutaneous Wound Healing*. J. Anat. 1999 November; 195 (Pt 4):531-42.

D. Rossi, Zlotnik, A. *The biology of chemokines and their receptors*. Annu. Rev. Immunol. 2000, 18, 217-242. 13.

D W H Riches, *Macrophage Involvement In Wound Repair, Remodeling and ®brosis. In The Molecular and Cellular*

*Biology of Wound Repair*, (1996) 1nd edn (ed. Clark R A F), pp. 95±141. New York, London: Plenum Press.

D. Greiling, et al., *Fibronectin Provides a Conduit for Fibroblast Transmigration from Collagenous Stroma into Fibrin Clot Provisional Matrix*. J. Cell. Sci. 1997; 110:861-70

M G Tonnesen, et al., *Angiogenesis In Wound Healing*. J. Investig. Dermatol. Symp. Proc. 2000; 5(1):40-6.

J P Kim, et al., *Mechanisms of Human Keratinocyte Migration on Fibronectin: Unique Role of RGD Site and Integrins*. J. Cell. Physiol. 1992; 151:443-50.

J J Tomasek et al., *Myofibroblasts and Mechano-Regulation of Connective Tissue Remodelling*. Nat. Rev. Mol. Cell. Biol. (2002) 3:349-363

S Werner, et al., *Regulation of Wound Healing by Growth Factors and Cytokines*. Physiol Rev. 2003 July; 83(3):835-70.

D. A. Keen, *Review of Research Examining the Regulatory Role of Lymphocytes in Normal Wound Healing*. J. Wound Care. 2008.

S. Liekens, et al., *Angiogenesis: regulators and clinical applications*. Biochem Pharmacol. 2001 Feb. 1; 61(3):253-70.

C. U. Niesler, & M. W. J. Ferguson. "*TGF-beta superfamily cytokines in wound healing*" in TGF-beta and Related Cytokines in Inflammation. Breit, S. N. and S. M. Wahl, ed., Birkhauser, Basel, 2001 pp. 173-198.

C. H. Heldin and B. Westermark. *Mechanism of action and in vivo role of platelet-derived growth factor*. Physiol Rev. 1999 October; 79(4):1283-316.

S. Blotnik, *T lymphocytes synthesize and export heparin-binding epidermal growth factor-like growth factor and basic fibroblast growth factor, mitogens for vascular cells and fibroblasts: differential production and release by CD41 and CD81 T cells*. Proc. Natl. Acad. Sci. USA 1994 91, 2890-2894.

B M Doshi, et al., *Wound Healing From a Cellular Stress Response Perspective*. Cell Stress Chaperones. 2008 December; 13(4):393-9.

G J Moran, et al., *Antimicrobial Prophylaxis for Wounds and Procedures in the Emergency Department*. Infect. Dis. Clin. North Am. 2008.

M A Fonder, et al., *Treating the Chronic Wound: A Practical Approach to the Care of Nonhealing Wounds and Wound Care Dressings*. J. Am. Acad. Dermatol. 2008 February; 58(2):185-206.

J A Thackham, et al., *The Use of Hyperbaric Oxygen Therapy to Treat Chronic Wounds: A Review*. Wound Repair Regen. 2008, 1998 May-June; 16(3):321-30.

D R Berlowitz, et al., *Are all pressure ulcers the result of deep tissue injury? A Review of the Literature*. Ostomy Wound Manage. 2007 October; 53(10):34-8.

K. Girouard, et al., *The symptom of pain with pressure ulcers: a review of the literature*. Ostomy Wound Manage. 2008 May; 54(5):30-40, 32.

Dumfarth, et al., Prophylactic low-energy shock wave therapy improves wound healing after vein harvesting for coronary artery bypass graft surgery: a prospective, randomized trial. Ann Thorac Surg. 2008 December; 86(6): 1909-13.

All publications cited in the specification, including both, patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A substantially cell-free activated leukocyte-conditioned supernatant (ALCS), wherein the ALCS is made by:
   incubating human leukocytes under conditions of time and temperature to activate the leukocytes, wherein the activated leukocytes comprise activated granulocytes, activated monocytes, and activated lymphocytes;
   subjecting the activated leukocytes to hypo-osmotic shock;
   adding to the activated leukocytes subjected to the hypo-osmotic shock to a physiologically acceptable solution containing inorganic ions, organic osmolytes, or a combination thereof in an amount which restores isotonicity;
   separating the activated leukocytes from the resulting isotonic solution;
   mixing the separated activated leukocytes with serum to form an incubation composition;
   incubating the incubation composition ii) at room temperature for 8 to 72 hours; or (ii) at about 37° C. for 3 to 5 hours; and
   separating the activated leukocytes and other cellular matter from the incubation composition to produce a substantially cell-free ALCS.

2. The substantially cell-free ALCS of claim 1, wherein the ALCS comprises at least about 1000 pg/mL human IL-8, at least about 10-20 pg/mL human IL-6, and at least about 20 pg/mL human TNFalpha.

3. An article of manufacture comprising the ALCS of claim 1 or 2, and a dressing, scaffold, or matrix.

4. The article of manufacture of claim 3, wherein:
   (i) the dressing is gauze, a bandage, a non-adhesive mesh, a membrane, foils, foam, or a tissue adhesive;
   (ii) the dressing is a moisture-keeping barrier;
   (iii) the dressing is a moisture keeping barrier selected from the group comprising a paste, a cream, an ointment, a nonpermeable or semi-permeable membrane or foil, a hydrocolloid, a hydrogel, and combinations thereof;
   (iii) the dressing is an antimicrobial dressing;
   (iv) the scaffold or matrix is a solid before implantation; and/or
   (v) the scaffold or matrix is a gel that solidifies following implantation.

5. A method for treating a wound or inhibiting the onset of infection in a wound comprising administering to the wound the ALCS of any one of claim 1 or 2.

6. The method of claim 5, wherein:
   (i) the wound is a decubital ulcer, a pressure ulcer, a lower extremity ulcer, tendonitis, a deep sternal wound, a post-operative wound, a refractory post-operative wound of the trunk area, a wound to the great saphenous vein following harvesting of the great saphenous vein, a venous ulcer, a burn wound, a battlefield wound, or an anal fissure;
   (ii) the wound is a lower extremity ulcer in a diabetic patient;
   (iii) the wound is a venous ulcer, pressure ulcer, or post-operative ulcer;
   (iv) the wound is caused by trauma;
   (v) the wound is caused by surgery;
   (vi) the ALCS is injected into the wound;
   (vii) the ALCS is injected into tissue surrounding the wound;

(viii) the wound is an open wound and the ALCS is applied into the open wound;
(ix) the wound is an open wound and the ALCS is applied to the open wound via a dressing,
(x) the wound is an open wound and the ALCS is applied to the open wound via a dry dressing, a barrier dressing, or a bioactive dressing;
(xi) the ALCS is derived from an autologous blood sample; and/or
(xii) the ALCS is derived from an allogeneic blood sample.

7. A method of making a substantially cell-free ALCS activated leukocyte-conditioned supernatant (ALCS), comprising:
    incubating human leukocytes under conditions of time and temperature to activate the leukocytes;
    subjecting the leukocytes to hypo-osmotic shock;
    adding to the leukocytes subjected to the hypo-osmotic shock to a physiologically acceptable solution containing inorganic ions, organic osmolytes, or a combination thereof in an amount which restores isotonicity;
    separating the leukocytes from the resulting isotonic solution;
    mixing the separated leukocytes with serum to form an incubation composition;
    incubating the incubation composition (i) at room temperature for 8 to 72 hours; or (ii) at about 37° C. for 3 to 5 hours; and
    separating the leukocytes and other cellular matter from the incubation composition to produce a substantially cell-free ALCS.

8. The method of claim 7, wherein the incubation of the human leukocytes to activate the leukocytes:
    (i) occurs at a temperature of about 12° C. to about 28° C. for a time ranging from about 8 to about 20 hours;
    (ii) occurs at a temperature of about 18° C. to about 24° C. for a time ranging from about 8 to about 12 hours;
    (iii) occurs at a temperature of 12° C. to about 28° C. for a time ranging from about 90 minutes upwards of 2, 3, 4, 5, 6, 7, 8, or 12 to about 20 hours; or
    (iv) occurs at a temperature up to about 37° C. and for a time ranging from 5 hours to about 24 hours.

9. The method of claim 4, wherein the subjecting the leukocytes to hypo-osmotic shock comprises contacting the leukocytes with water or a hypotonic salt solution for about 25 to about 45 seconds.

10. The method of claim 7, wherein:
    (i) the leukocytes and the serum are obtained from the same donor;
    (ii) the leukocytes and the serum are obtained from different donors;
    (iii) the serum of is obtained by contacting a separate sample of human plasma with a coagulating agent and removing coagulated solids;
    (iv) the serum is obtained by contacting a separate sample of human plasma with a coagulating agent and removing coagulated solids, wherein:
        (a) the plasma and the leukocytes are obtained from the same donor,
        (b) the plasma and the leukocytes are obtained from different donors,
        (c) the contacting of the human plasma with the coagulating agent is conducted substantially contemporaneously with the incubating of the human leukocytes under conditions of time and temperature to activate the leukocytes,
        (e) the plasma is obtained from an AB+ donor, and/or
        (f) the coagulating agent is $CaCl_2$;
    (v) the serum is frozen prior to contacting leukocytes; and/or
    (vi) the method further comprises freezing, lyophilizing, or freeze-drying the ALCS.

11. The method of claim 7, further comprising mixing and the leukocytes separated from the incubation composition with a second serum to form a second incubation composition; incubating the second incubation composition under conditions of time and temperature to increase the concentration of at least one cytokine or growth factor in the incubation composition; and separating the leukocytes and other cellular matter from the second incubation composition, so as to produce a second sample of the substantially cell-free ALCS.

12. The method of claim 7, wherein the incubation of the human leukocytes to activate the leukocytes is conducted in a container to which leukocytes adhere and/or which contains a scaffold comprising leukocyte agonists or adhesion molecules.

* * * * *